(12) United States Patent
Haramoto

(10) Patent No.: US 7,482,494 B2
(45) Date of Patent: Jan. 27, 2009

(54) BENZENE DERIVATIVE HAVING LONG, LINEAR CONJUGATED STRUCTURE, PROCESS FOR PRODUCING BENZENE DERIVATIVE, AND CHARGE-TRANSPORT MATERIAL

(75) Inventor: Yuichiro Haramoto, Kofu (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 147 days.

(21) Appl. No.: 10/548,387

(22) PCT Filed: Mar. 22, 2004

(86) PCT No.: PCT/JP2004/003859

§ 371 (c)(1),
(2), (4) Date: Jun. 23, 2006

(87) PCT Pub. No.: WO2004/085360

PCT Pub. Date: Oct. 7, 2004

(65) Prior Publication Data

US 2006/0255318 A1 Nov. 16, 2006

(30) Foreign Application Priority Data

Mar. 24, 2003 (JP) .............................. 2003-079714

(51) Int. Cl.
*C07C 41/09* (2006.01)
*C07C 43/205* (2006.01)
(52) U.S. Cl. ...................................... 568/629; 568/631
(58) Field of Classification Search ................. 558/275; 560/138
See application file for complete search history.

(56) References Cited

OTHER PUBLICATIONS

Wang et al., Gaodeng Xuexiao Huaxue Xuebao, 1980, 1(2), p. 125-7, Abstract from STN search report.*

* cited by examiner

*Primary Examiner*—Kamal A Saeed
*Assistant Examiner*—Yong Chu
(74) *Attorney, Agent, or Firm*—Westerman, Hattori, Daniels & Adrian, LLP.

(57) ABSTRACT

The present invention provides a benzene derivative having a long, linear conjugated structure, the benzene derivative being capable of exhibiting a satisfactory ability to transport charge without photoexcitation, a process for producing the benzene derivative, and a liquid-crystal material and a charge-transport material containing the benzene derivative having a long, linear conjugated structure. That is, a benzene derivative having a long, linear conjugated structure represented by general formula (1):

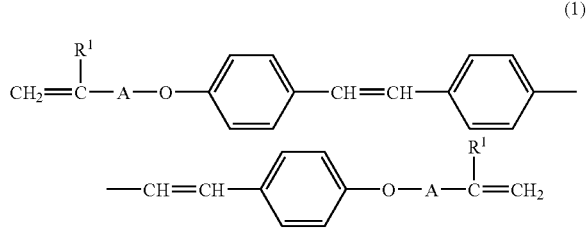

(1)

(wherein $R^1$ represents a methyl group or a hydrogen atom, A represents an alkylene group, $-CO-O-(CH_2)_n-$, $-C_6H_4-CH_2-$, or $-CO-$).

2 Claims, 9 Drawing Sheets

BENZENE DERIVATIVE HAVING LONG, LINEAR CONJUGATED STRUCTURE, PROCESS FOR PRODUCING BENZENE DERIVATIVE, AND CHARGE-TRANSPORT MATERIAL

This application is a U.S. continuation application filed under 35 USC 111(a) claiming benefit under 35 USC 120 and 365(c) of PCT application JP04/03859, filed Mar. 22, 2004, which claims priority to Application No. 2003-079714, filed in Japan on Mar. 24, 2003. The foregoing applications are hereby incorporated herein by reference.

TECHNICAL FIELD

The present invention relates to a novel benzene derivative having a long, linear conjugated structure, the benzene derivative being useful as a charge-transport material used in, for example, optical sensors, organic electroluminescent elements (EL elements), photoconductors, spatial modulators, thin-film transistors, charge-transport materials for electrophotographic photoreceptors, photolithography, solar cells, nonlinear optical materials, organic semiconductor capacitors, or other sensors. The present invention also relates to a liquid-crystal material, a charge-transport material, and a process for producing the benzene derivative.

BACKGROUND ART

In recent years, organic electroluminescent elements using organic materials as hole-transport materials or charge-transport materials constituting the electroluminescent elements have been intensively studied.

As such charge-transport materials, for example, anthracene derivatives, anthraquinoline derivatives, imidazole derivatives, styryl derivatives, hydrazone derivatives, triphenylamine compounds, poly(N-vinylcarbazoles), and oxadiazoles are known.

Liquid-crystal compounds have been used as materials for displays and applied to various devices, such as clocks, desktop electronic calculators, television sets, personal computers, and cellular phones. The liquid-crystal materials are classified into thermotropic liquid crystals (liquid crystals in which transitions depend on temperature) and lyotropic liquid crystals (liquid crystals in which transitions depend on concentration) on the basis of the mechanisms of phase transitions. From the standpoint of molecular arrangements, these liquid crystals are classified into three groups: smectic liquid crystals, nematic liquid crystals, and cholesteric liquid crystals. The liquid crystals are also known as anisotropic liquids and exhibit optical anisotropy similarly to optically uniaxial crystals. Observation using an orthoscope is usually performed between crossed Nicols, and is useful for the identification of types of liquid crystals and for the determination of the transition temperatures of liquid-crystal phases. The smectic liquid crystals are classified into A, B, C, D, E, F, and G on the basis of characteristic birefringent optical patterns observed with the orthoscope.

Hanna et al. have found that liquid-crystal compounds having smectic phases are capable of transporting charges and have proposed charge-transport materials using the liquid crystal compounds. They have proposed, for example, a liquid-crystalline charge-transport material exhibiting smectic liquid crystallinity and having a reduction potential of −0.3 to −0.6 (V vs. SCE) with reference to a standard calomel electrode (SCE) (Japanese Unexamined Patent Application Publication No. 09-316442); a liquid-crystalline charge-transport material including a liquid crystalline compound exhibiting a smectic phase having self-orientation properties and a predetermined amount of fullerene C70 having a sensitizing effect (Japanese Unexamined Patent Application Publication No. 11-162648); a polymer membrane in which a liquid-crystalline charge-transport material is dispersed in the polymer matrix, in other words, a polymer membrane in which a liquid-crystalline compound exhibiting a smectic phase is dispersed (Japanese Unexamined Patent Application Publication No. 11-172118); a liquid-crystalline charge-transport material including a mixture containing a smectic liquid-crystalline compound (Japanese Unexamined Patent Application Publication No. 11-199871); a liquid-crystalline charge-transport material having smectic liquid crystallinity and having an electron mobility or hole mobility of $1 \times 10^{-5}$ $cm^2/v \cdot s$ or more (Japanese Unexamined Patent Application Publication No. 10-312711); and a liquid-crystalline charge-transport material including a smectic liquid crystalline compound having, in one molecule, a functional group capable of forming a new intermolecular or intramolecular bond and a functional group capable of transporting a hole and/or electron (Japanese Unexamined Patent Application Publication No. 11-209761).

Smectic liquid-crystalline compounds disclosed in the above-described Patent Documents include smectic liquid-crystalline compounds each having a 6-π-electron aromatic ring such as a benzene ring, a pyridine ring, a pyrimidine ring, a pyridazine ring, a pyrazine ring, or a tropolone ring; smectic liquid-crystalline compounds each having a 10-π-electron aromatic ring such as a naphthalene ring, azulene ring, a benzofuran ring, an indole ring, an indazole ring, a benzothiazole ring, a benzoxazole ring, a benzimidazole ring, a quinoline ring, an isoquinoline ring, a quinazoline ring, or a quinoxaline ring; and smectic liquid-crystalline compounds each having a 14-π-electron aromatic ring such as a phenanthrene ring, or an anthracene ring. In these compounds, charges are transported in a smectic-A phase. However, the above-described method for transporting charges requires photoexcitation. Furthermore, conductivity is $10^{-13}$ s/cm without photoexcitation and $10^{-11}$ s/cm in a photoexcited state. The conductivity values are the same levels as those of an insulating material.

DISCLOSURE OF INVENTION

The present inventors have proposed a method for transporting charge by applying a voltage to a liquid-crystalline compound in a smectic-B phase or in a solid state due to phase transition from the smectic-B phase (Japanese Unexamined Patent Application Publication No. 2001-351786).

The present invention has been accomplished in view of such known techniques. It is an object of the present invention to provide a novel benzene derivative having a long, linear conjugated structure expected to have satisfactory charge-transport properties without photoexcitation, a process for producing the benzene derivative, and a liquid-crystal material and a charge-transport material including the benzene derivative.

A first aspect of the present invention provides a compound represented by general formula (1):

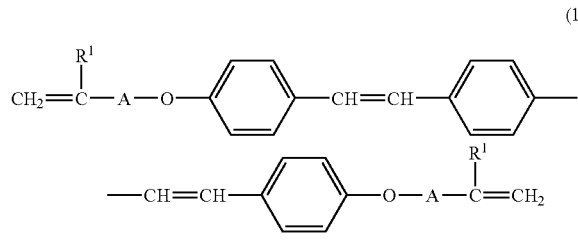

(wherein $R^1$ represents a methyl group or a hydrogen atom, and A represents an alkylene group, —CO—O(CH$_2$)$_n$—, —C$_6$H$_4$CH$_2$—, or —CO—).

A second aspect of the present invention provides a process for producing a benzene derivative having a long, linear conjugated structure represented by general formula (1):

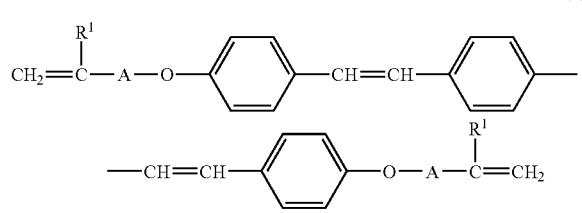

(wherein $R^1$ and A are the same as described above), the process including the steps of allowing 4-hydroxybenzaldehyde represented by general formula (2):

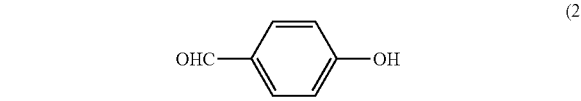

to react with a halogenated compound represented by general formula (3):

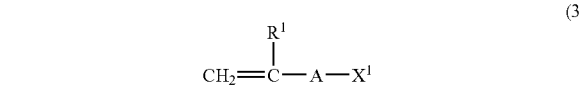

(wherein $R^1$ and A are the same as described above, and $X^1$ represents a halogen atom), in the presence of a base to produce a benzaldehyde derivative represented by general formula (4):

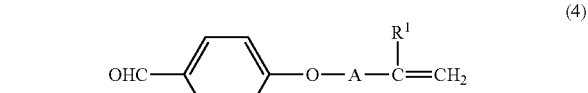

(wherein $R^1$ and A are the same as described above); and allowing the resulting benzaldehyde derivative to react with a p-xylenebis-(triphenylphosphonium halide) represented by formula (5):

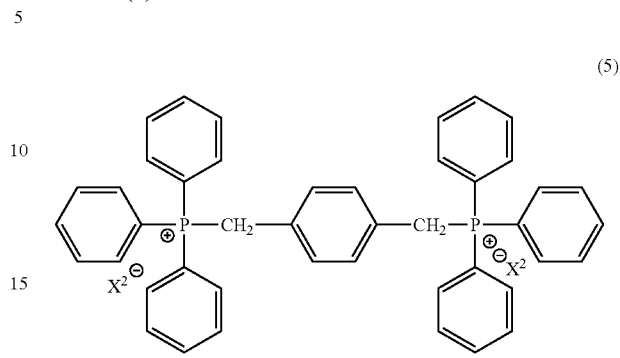

wherein $X^2$ represents a halogen atom.

A third aspect of the present invention provides a liquid-crystal material including a benzene derivative having a long, linear conjugated structure represented by general formula (1) described above or a compound derived from the benzene derivative.

A fourth aspect of the present invention provides a charge-transport material including the liquid-crystal material described above.

Figure 1:
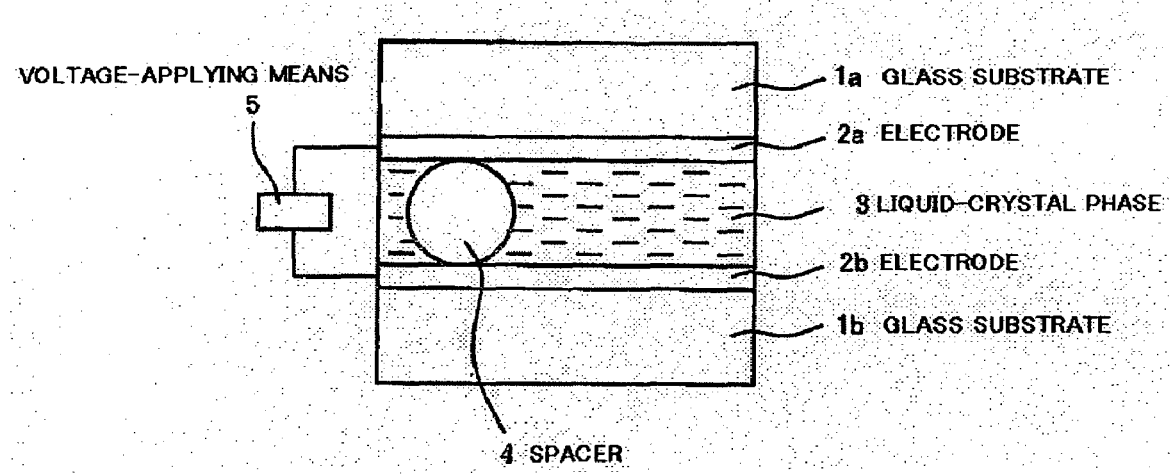
FIG. 1 is a schematic view of a charge-transport device, using an inventive charge-transport material, according to an embodiment of the present invention.

REFERENCE NUMERALS 1a, 1b glass substrate
2a, 2b electrode
4 spacer
3, 13 liquid-crystal layer
5 means for applying a voltage

BEST MODE FOR CARRYING OUT THE INVENTION

The present invention will be described in detail below.

$R^1$ in the benzene derivative having a long, linear conjugated structure represented by general formula (1) represents a hydrogen atom or a methyl group. A represents an alkylene group, —CO—O—$(CH_2)_n$—, —$C_6H_4$—$CH_2$—, or —CO—. The alkylene group may be straight or branched chain and preferably has 1 to 18 carbon atoms. Examples thereof include a methylene group, an ethylene group, a trimethylene group, a tetramethylene group, a pentamethylene group, an ethylethylene group, a propylene group, a butylene group, a hexylene group, an octadecylene group, a nonylene group, a decylene group, and a dodecylene group. Furthermore, n in —CO—O—$(CH_2)_n$— is particularly preferably 1 to 18.

In the present invention, a benzene derivative having a long, linear conjugated structure represented by general formula (1) is a novel compound. With respect to a conformation, the benzene derivative may be a cis-isomer, a trans-isomer, or a mixture of cis- and trans-isomers.

A process for producing a benzene derivative having a long, linear conjugated structure represented by general formula (1) will be described below.

The production process according to the present invention basically includes a first step and a second step described below.

<First Step>

The first step is a step of producing a benzaldehyde derivative represented by general formula (4), the benzaldehyde derivative being prepared by the reaction shown in reaction formula (1):

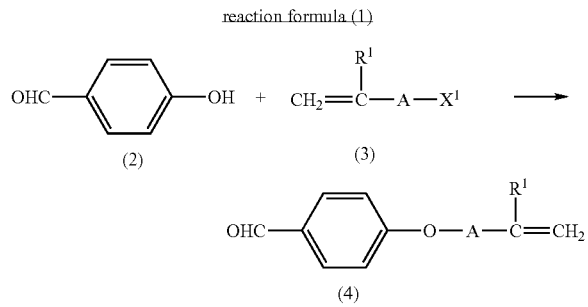

(wherein $R^1$, A and $X^1$ are the same as described above).

Here, 4-hydroxybenzaldehyde, which is a first material used in the first step, represented by general formula (2) is not limited but may be commercially available.

$R^1$ and A in a halogenated compound, which is a second material used in the first step, represented by general formula (3) correspond to $R^1$ and A, respectively, in the benzene derivative having a long, linear conjugated structure represented by general formula (1). $R^1$ represents a hydrogen atom or a methyl group. A represents an alkylene group, —CO—O—$(CH_2)_n$—, —$C_6H_4$—$CH_2$—, or —CO—. The alkylene group may be straight or branched chain and preferably has 1 to 18 carbon atoms. Examples thereof include a methylene group, an ethylene group, a trimethylene group, a tetramethylene group, a pentamethylene group, an ethylethylene group, a propylene group, a butylene group, a hexylene group, an octadecylene group, a nonylene group, a decylene group, and a dodecylene group. Furthermore, n in —CO—O—$(CH_2)_n$— is particularly preferably 1 to 18.

$X^1$ represents a halogen atom such as chlorine, bromine, or iodine. From the standpoint of reactivity, bromine atom is particularly preferable.

The halogenated compound, which is the second material, represented by general formula (3) may be produced by a known method. For example, the target halogenated compound (compound (3)) can be easily produced by the reaction of equimolar amounts of an alcohol (compound (5)) and a phosphorus halide (compound (6)) in a solvent, such as benzene, in the presence of a base, such as pyridine, at about 20° C. for about 18 hours, the reaction being represented by reaction formula (2):

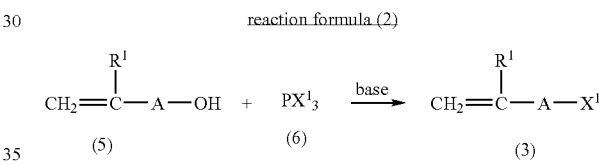

(wherein $R^1$, A and $X^1$ are the same as described above). The reaction is preferably performed in the presence of a polymerization inhibitor, such as phenothiazine.

In the first step, 4-hydroxybenzaldehyde represented by general formula (2) is allowed to react with a halogenated compound represented by general formula (3) in a solvent in the presence of a base.

Here, 1 or more and preferably 1.5 to 2.0 moles of the halogenated compound represented by general formula (3) is added per mole of 4-hydroxybenzaldehyde represented by general formula (2).

Examples of the base that can be used include, but are not limited to, inorganic bases such as sodium hydroxide, sodium carbonate, sodium hydrogencarbonate, potassium hydroxide, potassium carbonate, potassium hydrogencarbonate, calcium hydroxide, calcium carbonate, barium hydroxide, and calcium hydroxide; organic bases such as trimethylamine, N,N-dimethylcyclohexylamine, N,N-diethylcyclohexylamine, N,N-dimethylbenzylamine, N,N'-dimethylpiperazine, N,N-dimethylaniline, N,N-diethylaniline, N,N,N',N'-tetramethyl-1,3-propanediamine, pyridine, α-picoline, β-picoline, γ-picoline, 4-ethylmorpholine, triethylenediamine, 1,3-diazabicyclo[5,4,0]undecene, 1,8-diazabicyclo[5,4,0]-7-undecene, N-ethylpiperidine, quinoline, isoquinoline, N,N-dimethylpiperazine, N,N-diethylpiperazine, quinaldine, 2-ethylpyridine, 4-ethylpyridine, 3,5-lutidine, 2,6-lutidine, 4-methylmorpholine, and 2,4,6-collidine; and ion-exchange resins containing a pyridyl group and dimethylaminobenzyl group. These may be used alone or in combination of two or more.

The amount of base added is usually equimolar to 4-hydroxybenzaldehyde represented by general formula (2), and this amount is sufficient.

Examples of the reaction solvent include ethers such as dioxane, tetrahydrofuran, and dibutyl ether; nitrites such as acetonitrile and propionitrile; alcohols such as methanol and ethanol; and other compounds such as dimethylformamide, acetone, and water. These may be used alone or in combination of two or more.

With respect to reaction conditions, the reaction temperature is 0° C. to 100° C. and preferably 20° C. to 50° C., and the reaction time is 0.5 to 50 hours and preferably 10 to 30 hours.

After the reaction, various procedures, such as washing with an acid, extraction, washing, dehydration, recrystallization, and column chromatography are performed. Thereby the benzaldehyde represented by general formula (4) is produced.

<Second Step>

A second step is a step of producing a benzene derivative having a long, linear conjugated structure represented by general formula (1) by the reaction represented by reaction formula (3):

hydride; amines such as trimethylamine and triethylamine; alkali hydroxides such as potassium hydroxide and sodium hydroxide; alkoxides such as sodium methoxide, potassium methoxide, sodium ethoxide, and potassium ethoxide; and other compounds such as piperidine, pyridine, potassium cresolate, and alkyllithium. These compounds may be used alone or in combination of two or more.

Here, 1 to 5 and preferably 3.5 to 4.5 moles of the base is added per mole of p-xylenebis-(triphenylphosphonium halide) represented by general formula (5).

Examples of the reaction solvent include ethers such as dioxane, tetrahydrofuran, and dibutyl ether; nitrites such as acetonitrile and propionitrile; alcohols such as methanol and ethanol; and other compounds such as dimethylformamide and acetone. These may be used alone or in combination of two or more.

With respect to reaction conditions, the reaction temperature is 0° C. to 100° C. and preferably 20° C. to 50° C. The reaction time is 0.5 to 50 hours and preferably 5 to 30 hours.

After the reaction, if necessary, purification, such as washing or recrystallization, is performed to produce a benzene

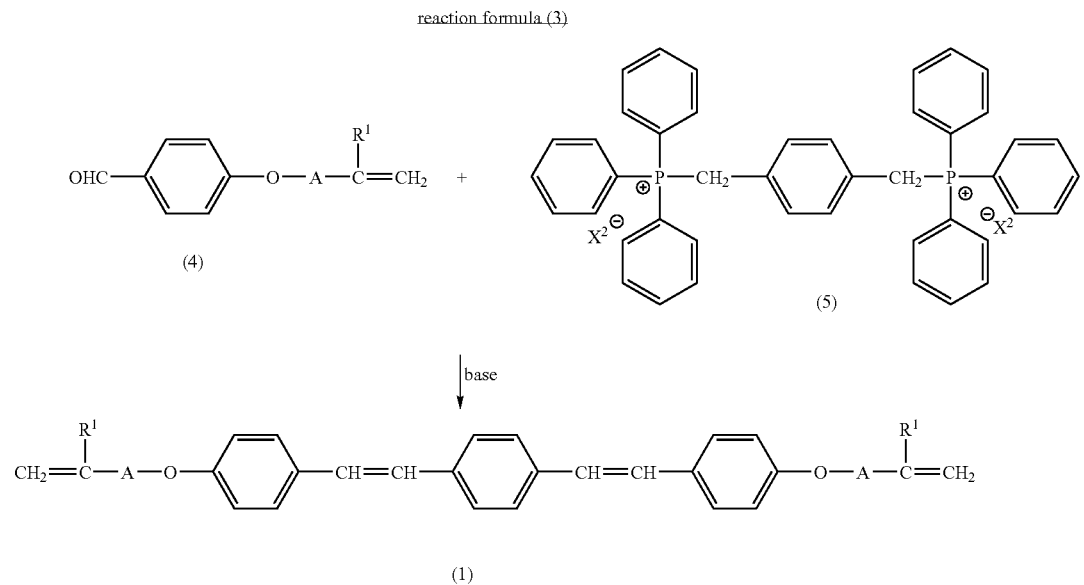

reaction formula (3)

(wherein $R^1$, A and $X^2$ are the same as described above).

$X^2$ in the p-xylenebis-(triphenylphosphonium halide) represented by general formula (5) represents a halogen atom such as chlorine, bromine, or iodine. From the standpoint of reactivity, bromine is particularly preferable. The p-xylenebis-(triphenylphosphonium halide) may be commercially available.

In the second step, the benzaldehyde derivative represented by general formula (4) is allowed to react with the p-xylenebis-(triphenylphosphonium halide) represented by general formula (5) in a solvent in the presence of a base.

Here, 2 to 4 and preferably 2 to 2.5 moles of the p-xylenebis-(triphenylphosphonium halide) represented by general formula (5) is added per mole of the benzaldehyde derivative represented by general formula (4).

Examples of the base that can be used in the second step include, but are not limited to, metal hydride such as sodium derivative having a long, linear conjugated structure represented by general formula (1).

In the production process according to the present invention, if necessary, the benzene derivative having a long, linear conjugated structure represented by general formula (1) may be heat-treated in a solvent in the presence of iodine.

The trans-isomer of the benzene derivative having a long, linear conjugated structure represented by general formula (1) can be selectively produced by this heat treatment.

In this case, 0.001 to 0.1 and preferably 0.005 to 0.01 moles of iodine is added per mole of the benzene derivative having a long, linear conjugated structure represented by general formula (1). The heating temperature is 100° C. to 180° C. and preferably 130° C. to 150° C. Examples of a solvent that can be used include benzene, toluene, o-xylene, m-xylene, p-xylene, chlorobenzene, o-dichlorobenzene, m-dichlorobenzene, and p-dichlorobenzene. These solvents may be used alone or in combination of two or more.

The resulting benzene derivative having a long, linear conjugated structure represented by general formula (1) is a novel compound and capable of transporting charge. The benzene derivative also exhibits liquid crystallinity and blue-light emission. By using charge transportability, the benzene derivative can be used for a charge-transport material used in, for example, optical sensors, organic electroluminescent elements (EL elements), photoconductors, spatial modulators, thin-film transistors, charge-transport substances for electrophotographic photoreceptors, photolithographic materials, solar cells, nonlinear optical materials, organic semiconductor capacitors, or other sensors.

Next, the liquid-crystal material according to the present invention will be described.

The liquid-crystal material according to the present invention includes the benzene derivative having a long, linear conjugated structure represented by general formula (1) or a compound derived from the benzene derivative having a long, linear conjugated structure.

The term "compound derived from the benzene derivative having a long, linear conjugated structure represented by general formula (1)" (hereinafter, referred to as "polymer") means a homopolymer or copolymer of the benzene derivative; a polymeric compound cross-linked with the benzene derivative using a cross-linking agent; or a polymeric compound prepared by addition reaction of the benzene derivative with a hydrosilyl group-containing polymeric compound.

Here, the polymer includes at least a repeating unit represented by general formula (7) or (8):

ence of a polymerization initiator by radical polymerization such as solution polymerization, suspension polymerization, emulsion polymerization, or bulk polymerization.

Furthermore, in order to produce a polymeric compound by addition reaction of a hydrosilyl group-containing polymeric compound with the benzene derivative having a long, linear conjugated structure represented by general formula (1), the hydrosilyl group-containing polymeric compound is allowed to react with the benzene derivative having a long, linear conjugated structure represented by general formula (1) in the presence of platonic chloride, a platonic chloride alcohol solution, a complex of platinum and an olefin complex, or a rhodium catalyst such as a rhodium carbonyl complex.

The liquid-crystal material according to the present invention is a material exhibiting smectic liquid crystallinity and including the benzene derivative having a long, linear conjugated structure represented by general formula (1), a composition containing the benzene derivative having a long, linear conjugated structure, the above-described polymer, or a composition containing the polymer.

In the composition containing the benzene derivative having a long, linear conjugated structure represented by general formula (1), the content of the benzene derivative having a long, linear conjugated structure represented by general formula (1) is at least 30 percent by weight or more, preferably 50 percent by weight or more, and most preferably 90 percent by weight or more. Furthermore, the composition exhibits smectic liquid crystallinity due to the liquid-crystalline compound having a long, linear conjugated structure represented by general formula (1).

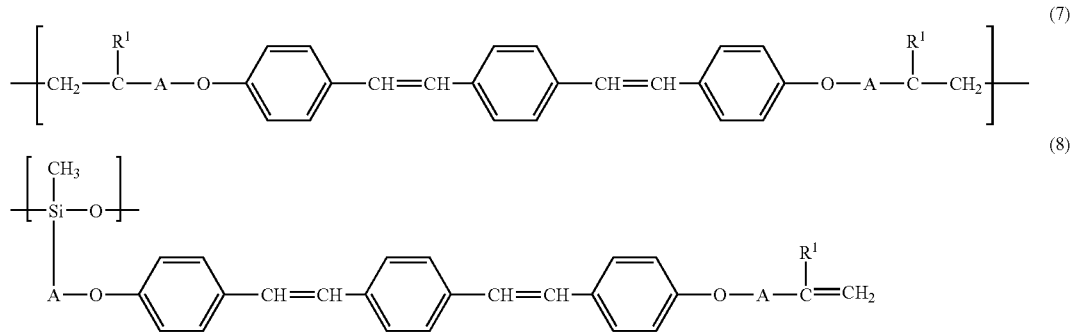

(wherein $R^1$ and A are the same as described above)

The polymer may include a repeating unit, which is a copolymer component, derived from, for example, acrylic acid, methacrylic acid, or styrene. When the polymer is a copolymer, the content of the repeating unit represented by general formula (7) or (8) is 50 mole percent or more, preferably 70 mole percent or more, and most preferably 80 mole percent or more.

The number-average molecular weight of the polymer is in the range of 1,000 to tens of millions and preferably tens of thousands to millions.

The polymer can be produced by the following method. For example, in order to produce a homopolymer or copolymer of the benzene derivative represented by general formula (1) or a polymeric compound cross-linked with the benzene derivative using a cross-linking agent, either a predetermined monomer alone or a mixture of a predetermined monomer with a cross-linking agent may be polymerized in the pres- The other components in the composition are used for adjusting the phase transition temperature of the benzene derivative having a long, linear conjugated structure represented by general formula (1). For example, other liquid-crystalline compounds or other compounds each having a long, linear conjugated structure and having an alkyl group or an alkoxide group at its ends may be used alone or in combination of two or more. The other compounds each having a long, linear conjugated structure and having an alkyl group or an alkoxide group at its ends may be a liquid-crystalline compound or not. These other components may be used alone or in combination of two or more.

The composition containing the benzene derivative having a long, linear conjugated structure represented by general formula (1) can be prepared as follows: the benzene derivative having a long, linear conjugated structure represented by general formula (1) and a predetermined component described above are dissolved in a solvent, and then the solvent is removed by heating, under a reduced pressure, or the like; the benzene derivative having a long, linear conjugated structure represented by general formula (1) and a predetermined component described above are mixed and melted by heating; or sputtering, vacuum evaporation, or the like.

In the composition containing the polymer, the content of the polymer is at least 30 percent by weight or more, preferably 50 percent by weight or more, and most preferably 80 percent by weight or more. Furthermore, the composition exhibits smectic liquid crystallinity due to the liquid-crystallinity of the benzene derivative having a long, linear conjugated structure represented by general formula (1).

The other components in the composition are used for adjusting the phase transition temperature of the polymer. For example, other liquid-crystalline compounds or other compounds each having a long, linear conjugated structure and having an alkyl group or an alkoxide group at its ends may be used alone or in combination of two or more. The other compounds each having a long, linear conjugated structure and having an alkyl group or an alkoxide group at its ends may be a liquid-crystalline compound or not. These other components may be used alone or in combination of two or more.

The composition containing the polymer can be prepared as follows: the polymer and a predetermined component described above are dissolved in a solvent, and then the solvent is removed by heating, under a reduced pressure, or the like; the polymer and a predetermined component described above are mixed and melted by heating; or sputtering, vacuum evaporation, or the like.

The liquid-crystal material according to the present invention can be used as a charge-transport material capable of satisfactorily transporting charge by applying a voltage to the liquid-crystal material in a liquid-crystalline state or in a solid state due to phase transition of the liquid-crystalline state.

In preferred examples of the inventive benzene derivative having a long, linear conjugated structure represented by general formula (1), $R^1$ represents a hydrogen atom or a methyl group, A represents a straight alkylene group having 6 to 18 and preferably 8 to 12 carbon atoms, $-C_6H_4-CH_2-$, $-CO-$, or $-CO-O-(CH_2)_n-$, and n is 6 to 18 and preferably 8 to 12.

The charge-transport material according to the present invention contains the liquid-crystal material. The liquid-crystal material according to the present invention has a smectic phase as its liquid-crystal phase.

In the charge-transport material according to the present invention, a charge is transported by applying a voltage to the liquid-crystal material in a smectic liquid-crystalline state or in a solid state, such as a crystalline phase, a glass state, or an amorphous solid, due to phase transition during cooling from a smectic phase.

When the liquid-crystal material is used in a solid state, the molecular orientation of the smectic phase can be maintained in the case in which slow cooling is performed compared with the case in which rapid cooling is performed. Therefore, when slow cooling is performed, the charge-transport material has a satisfactory ability to transport charge compared with the case in which rapid cooling is performed.

The charge-transport material according to the present invention can be used as, for example, a charge-transport device. The charge-transport device (hereinafter referred to as "first charge-transport device) includes a liquid-crystal layer composed of the charge-transport material, two substrates each having an electrode, the liquid-crystal layer being disposed between the two substrates, and means for transporting charge through the charge-transport material by applying a voltage to the charge-transport material in a smectic liquid-crystalline state. Alternatively, The charge-transport device (hereinafter referred to as "second charge-transport device) includes a liquid-crystal layer composed of the charge-transport material, two substrates each having an electrode, the liquid-crystal layer being disposed between the two substrates, and means for transporting charge through the charge-transport material by applying a voltage to the charge-transport material in a solid state due to phase transition from a smectic phase.

FIG. 1 is a schematic view of the first charge-transport device according to an embodiment of the present invention. The first charge-transport device shown in FIG. 1 is produced as follows: electrodes 2a and 2b composed of transparent material, such as ITO, is formed on the surfaces of two glass substrates 1a and 1b, respectively. The two substrates having the electrodes are bonded to each other with a spacer 4 using an adhesive so as to keep the distance between the substrates constant to form a cell. The charge-transport material is introduced into the cell to form a liquid-crystal layer 3 between the electrodes. Applying a voltage to the electrodes 2a and 2b in a smectic liquid-crystalline state of the charge-transport material results in high current density through the liquid-crystal layer, thereby permitting charge transport.

Figure 2:
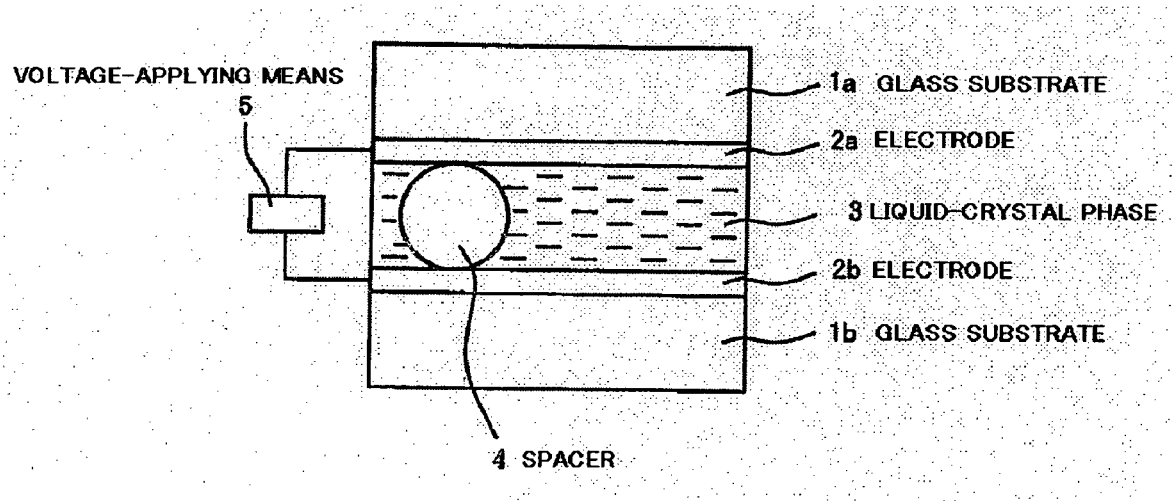
FIG. 2 is a schematic view of a charge-transport device, using an inventive charge-transport material, according to an embodiment of the present invention.

FIG. 2 is a schematic view of the second charge-transport device according to an embodiment of the present invention. The second charge-transport device shown in FIG. 2 is produced as follows: electrodes 2a and 2b composed of transparent material, such as ITO, is formed on the surfaces of two glass substrates 1a and 1b, respectively. The two substrates having the electrodes are bonded to each other with a spacer 4 using an adhesive so as to keep the distance between the substrates constant to form a cell. The charge-transport material is introduced into the cell to form a liquid-crystal layer 13 between the electrodes. A voltage-applying means 5 for applying a voltage to the electrodes 2a and 2b in a solid state due to phase transition from a smectic phase of the charge-transport material are connected to the electrodes 2a and 2b. Applying a voltage to the charge-transport material of the liquid-crystal layer 13 with charge-transport means including the voltage-applying means and thermoregulating means (not shown) in a solid state due to phase transition from a smectic phase of the charge-transport material results in high current density through the liquid-crystal layer, thereby permitting charge transport.

The inventive benzene derivative having a long, linear conjugated structure represented by general formula (1) is a liquid-crystalline compound. By Using molecular orientation of a smectic phase, having a laminar arrangement of molecules, in a smectic liquid-crystalline state or a solid state due to phase transition resulting from cooling of a smectic phase, long conjugated π-electron systems of the liquid-crystalline compound overlap densely. Charge can be transported at a current density of the order of 500 $\mu A/cm^2$ or more and preferably the order of 1 $mA/cm^2$ or more. By using such charge-transport properties, the benzene derivative can be suitably used as a charge-transport material used in, for example, optical sensors, organic electroluminescent elements (EL elements), photoconductors, spatial modulators, thin-film transistors, charge-transport substances for electrophotographic photoreceptors, photolithographic materials, solar cells, nonlinear optical materials, organic semiconductor capacitors, or other sensors.

For example, when the inventive charge-transport material is used for an organic electroluminescent element (EL element), the charge-transport material serving as a luminescent layer may contain another luminescent material, if necessary. The EL element may be produced by interposing the luminescent layer between two electrodes (at least one electrode is composed of a transparent material, such as ITO). Furthermore, for laminated organic luminescent element, the inventive charge-transport material may be used as a hole-transport layer, an electron-transport layer, or a luminescent layer. For a optical sensor, a change in current due to light irradiation can be detected by interposing the inventive charge-transport material between two electrodes (at least one electrode is transparent). When the charge-transport material is used for an electrophotographic photoreceptor or an image-storage element, a charge-generating layer and the conductivity-type layer according to the present invention may be stacked on a substrate or an electrode.

EXAMPLES

While the present invention will be described in detail below, it is understood that the invention is not limited thereto.

Example 1

<First Step>

According to reaction formula (4), p-9-(decenoxy)-benzaldehyde (compound (12)) was synthesized.

reaction formula (4)

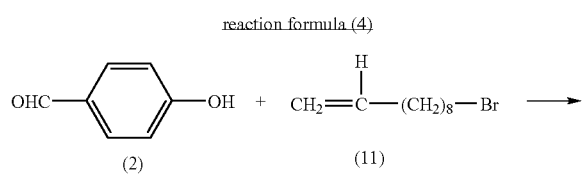

-continued

OHC—⟨benzene⟩—O—(CH$_2$)$_8$—C(H)=CH$_2$ (12)

To a solution prepared by dissolving 2.44 g (0.02 mol) of 4-hydroxybenzaldehyde (compound (2)) in 30 mL of ethanol, 50 mL of an ethanol solution containing 1.12 g (0.02 mol) of potassium hydroxide was added. The resulting mixture was stirred, and ethanol was removed under reduced pressure with an evaporator. The resulting residue was dissolved in 50 mL of DMF, and 10 mL of a DMF solution containing 6.57 g (0.03 mol) of 10-bromo-1-decene (compound (11)) was added dropwise thereto. The reaction was performed at 70° C. for 15 hours in an nitrogen atmosphere. After the reaction, the reaction mixture was cooled to room temperature and fed into diluted hydrochloric acid under ice cooling. Subsequently, diethyl ether was added thereto, and extraction was performed. After the resulting extract was dried over anhydrous sodium sulfate overnight, anhydrous sodium sulfate was removed by filtration. Diethyl ether was removed with an evaporator. Isolation was performed by column chromatography with removed diethyl ether as a solvent, followed by drying. Thereby, 3.62 g of a pale yellow liquid of target p-9-(decenoxy)-benzaldehyde (compound (12)) was produced (yield: 69.5%).

<Identification Data>

$^1$H-NMR (δ, CDCl$_3$):

0.8-2.0 (m, 14H, —(CH$_2$)$_7$—), 4.0 (t, 2H, —O—CH$_2$—), 4.9-5.1 (d, 2H, —C=CH$_2$), 5.3-6.2 (m, 1H, —CH=C), 7.0, 7.9 (d, 4H, aromatic), 10 (s, 1H, —CHO).

<Second Step>

In a second step, according to reaction formula (5):

reaction formula (5)

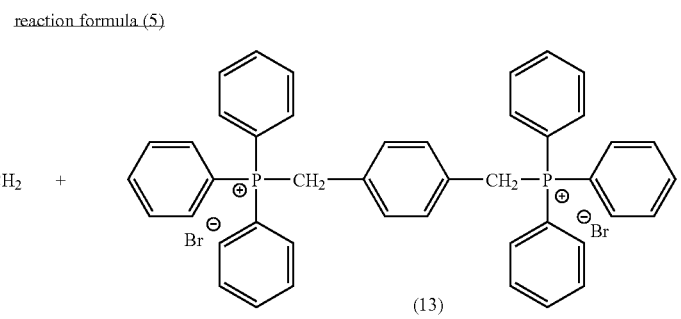

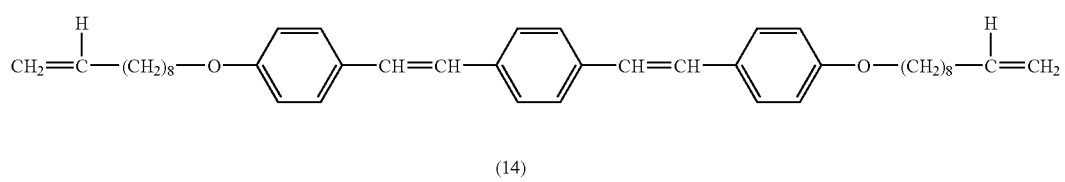

a benzene derivative (compound (14)) having a long, linear conjugated structure was synthesized.

To 50 mL of a ethanol solution containing 2.60 g (0.01 mol) of p-9-(decenoxy)-benzaldehyde prepared in the first step and 3.93 g (0.005 mol) of p-xylenebis-(triphenylphosphonium bromide) (compound (13), manufactured by Tokyo Kasei Kogyo Co., Ltd.), 50 mL of sodium ethoxide (0.4 mol) was added dropwise thereto. After the resulting mixture was stirred at room temperature for 30 minutes, the reaction was performed at 50° C. for 10 hours. The reaction mixture was filtrated, and then the resulting precipitate was washed with 60% aqueous ethanol and hexane, followed by drying. Thereby, 1.10 g of a pale yellow solid of a target benzene derivative having a long, linear conjugated structure (compound (14)) was produced (yield: 18.6%).

<Identification Data>
Melting point: 85° C.-87° C.
$^1$H-NMR ($\delta$, $CDCl_3$):
1.2-1.5 (m, 16H), 1.6-1.7 (m, 4H), 1.7-1.8 (m, 4H), 2.0-2.1 (m, 4H), 3.9-4.0 (t, 4H), 4.9-5.1 (d, 4H), 5.7-5.9 (m, 2H), 6.8 (d, 4H), 6.9-7.1 (m, 4H), 7.2-7.5 (m, 8H).
IR ($cm^{-1}$, KBr).
721 (p-ph out-of-plane deformation vibration), 968 (t-C=C— out-of-plane deformation vibration), 1,110-1,253 (C—O—C stretching vibration), 1,465-1,573 (ph skeletal vibration), 1,641 ($CH_2$=CH— stretching), 2,852-2,921 (aliphatic CH stretching), 3,021-3,075 (aromatic CH stretching).
MASS (FAB: Xe): 590 (M-1).

Example 2

A benzene derivative represented by general formula (15) was prepared as in EXAMPLE 1 including the first and second steps, except that 8-bromo-1-octene was used instead of 10-bromo-1-decene.

<Identification Data>
$^1$H-NMR ($\delta$, $CDCl_3$): 1.2-1.5 (m, 12H) , 1.6-1.7 (m, 4H), 2.0-2.1 (m, 4H), 3.9-4.0 (t, 4H), 4.9-5.1 (d, 4H), 5.7-5.9 (m, 2H), 6.8 (d, 4H), 6.9-7.1 (m, 4H), 7.2-7.5 (m, 8H).

MASS (FAB: Xe): 534 (M-1).
IR (KBr, cm-1): 3,075-3,021 (aromatic C—H stretching vibration), 2,921-2,852 (aliphatic C—H stretching vibration), 1,641 (CH2=CH— stretching vibration), 1,573-1,465 (ph skeletal vibration), 1,253-1,110 (C—O—C stretching vibration), 968 (t-C=C— out-of-plane deformation), 721 (aromatic C—H out-of-plane deformation vibration).

Furthermore, the benzene derivatives prepared in EXAMPLES 1 and 2 were analyzed by X-ray diffraction, and the textures of the benzene derivatives were observed with a polarizing microscope. The results indicated phase transitions as shown in Table 1.

TABLE 1

| | Phase transition |
|---|---|
| EXAMPLE 1 | Cyst ⇌ 100° C. SmG ⇌ 220° C. SmB ⇌ 225° C. SmA ⇌ 260° C. Iso |
| EXAMPLE 2 | Cyst ⇌ 107° C. SmG ⇌ 192° C. Iso |

Figure 3:
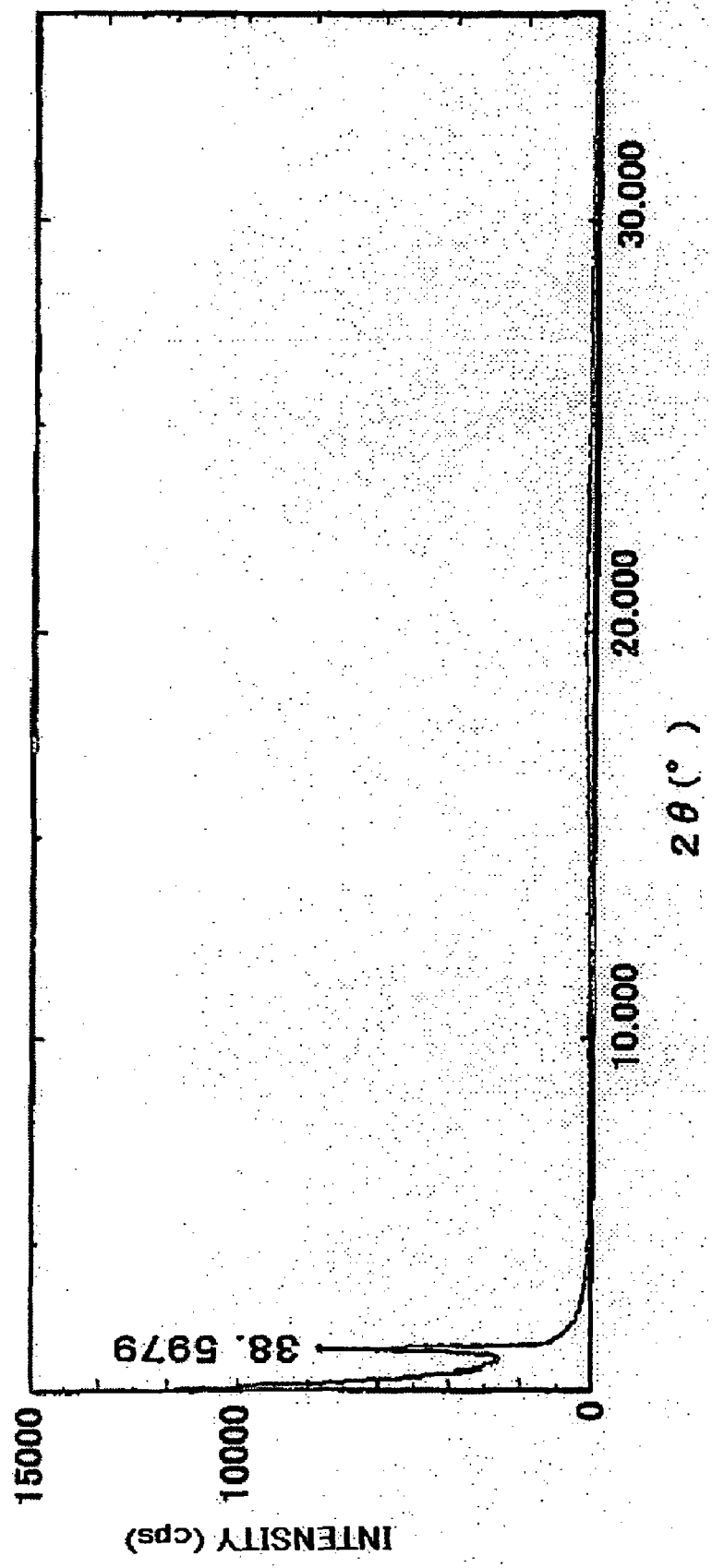
FIG. 3 is an X-ray diffraction pattern, recorded at 170° C., of a benzene derivative having a long, linear conjugated structure prepared in EXAMPLE 1.

Cyst: crystal, SmG smectic-G phase, SmB: smectic-B phase, SmB: smectic-A phase, Iso: isotropic liquid FIG. 3 is an X-ray diffraction pattern, recorded at 170° C., of the benzene derivative (compound (14)) prepared in EXAMPLE 1.

Figure 4:
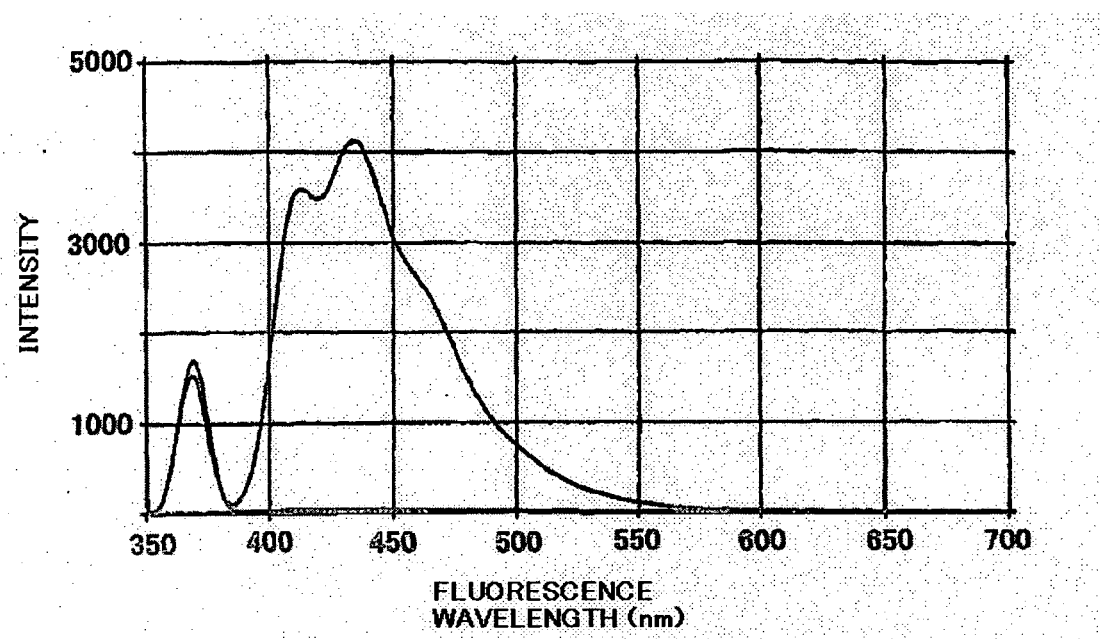
FIG. 4 is a fluorescence spectrum of the benzene derivative, excited at a wavelength of 368 nm, having a long, linear conjugated structure prepared in EXAMPLE 1.

FIG. 4 is a fluorescence spectrum of the benzene derivative, excited at a wavelength of 368 nm, (compound (14)) prepared in EXAMPLE 1.

<Evaluation of Ability to Transport Charge>

Two glass substrate each having an ITO electrode formed by vacuum film deposition were bonded to each other in a manner such that the electrodes faced each other and such that the gap (about 15 μm) between the electrodes was formed with spacer particles, thereby producing a cell.

At 230° C., 20 mg of the benzene derivative having a long, linear conjugated structure represented by general formula (1) prepared in EXAMPLE 1 was introduced into the cell.

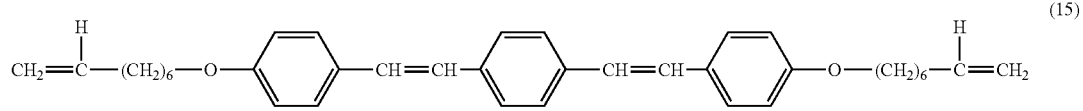

(15)

Figure 5:
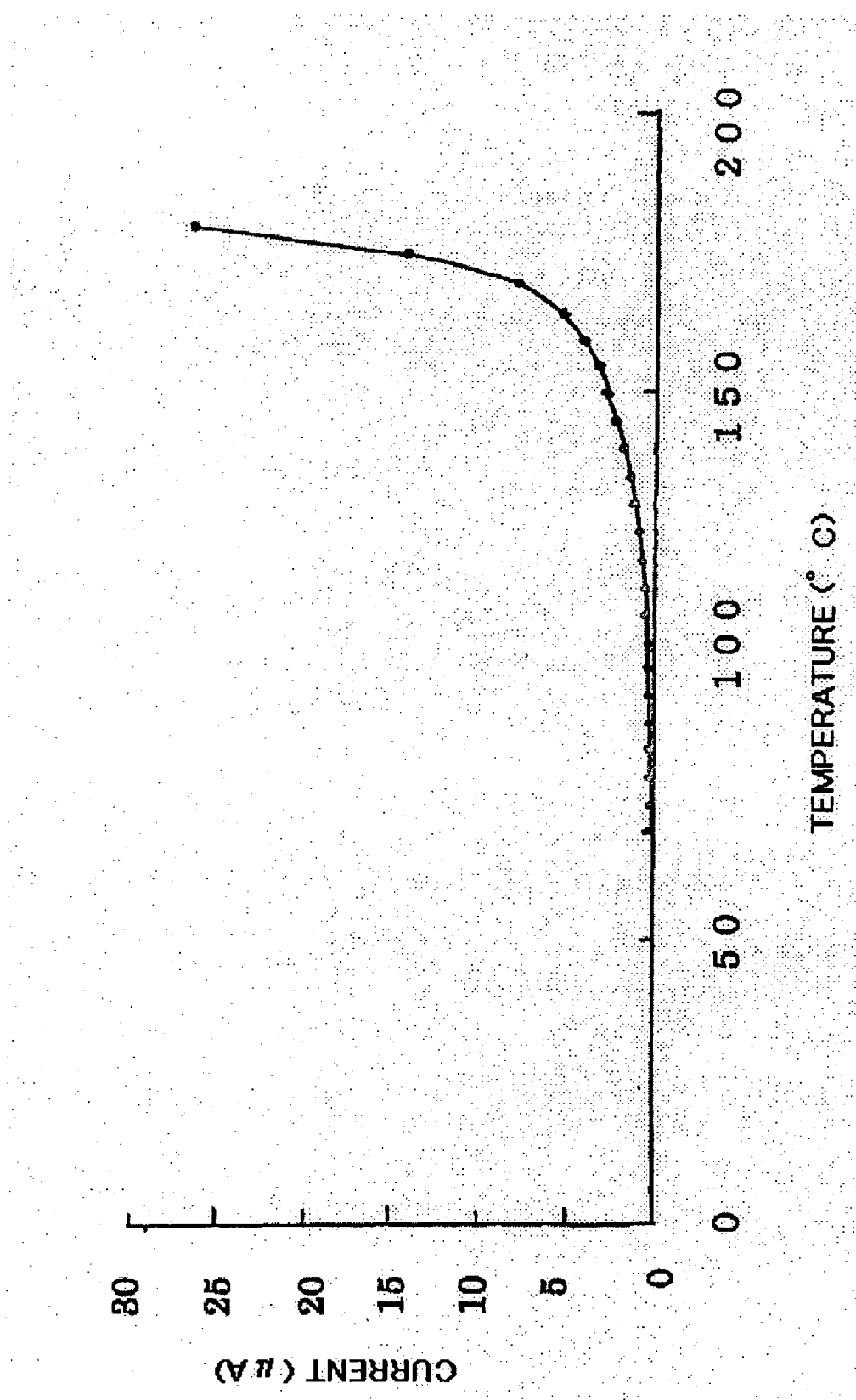
FIG. 5 is a graph showing the relationship between temperature and current when the benzene derivative having a long, linear conjugated structure prepared in EXAMPLE 1 is gradually heated at an applied voltage of 5 V.

The cell was gradually heated at an applied voltage of 5 V, and current was measured at each temperature. FIG. 5 shows the results.

Figure 6:
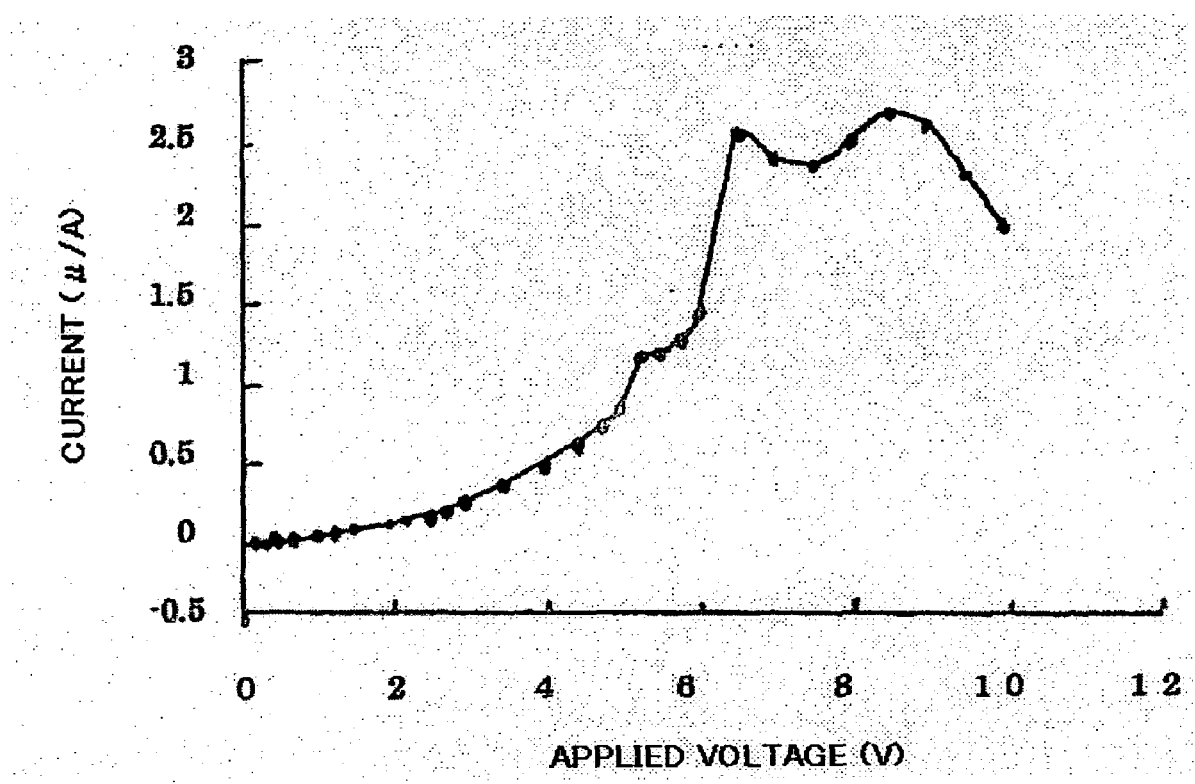
FIG. 6 is a graph (first time) showing the relationship between voltage and current when the temperature of the benzene derivative having a long, linear conjugated structure prepared in EXAMPLE 1 is maintained at 130° C.
Figure 7:
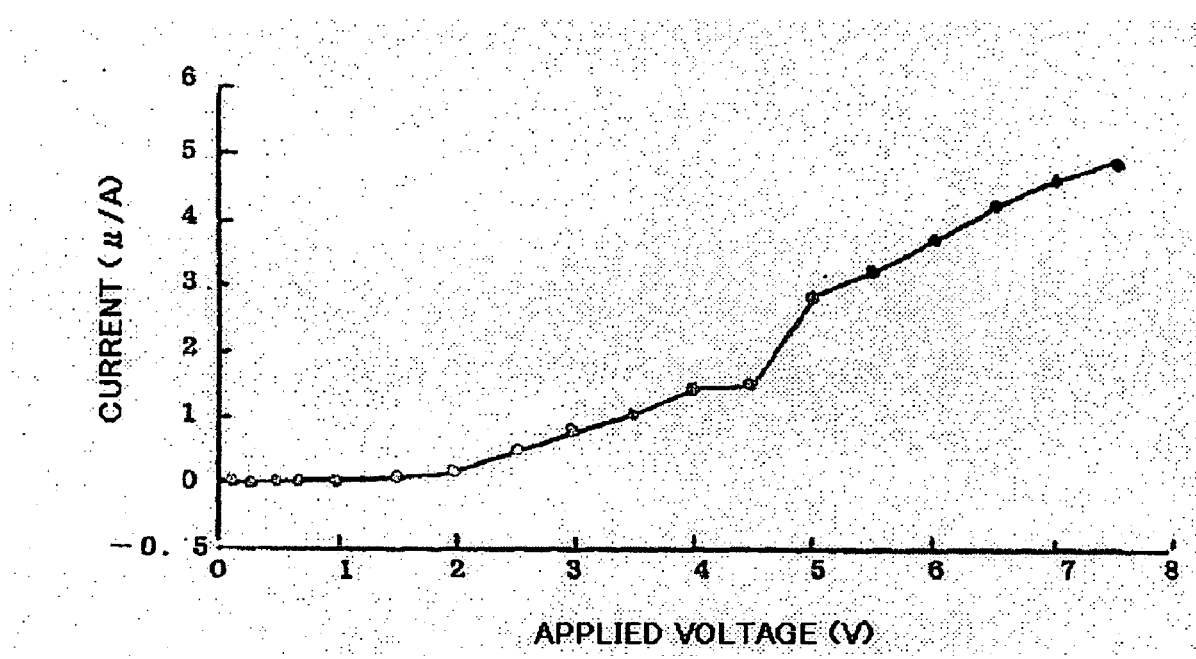
FIG. 7 is a graph (second time) showing the relationship between voltage and current when the temperature of the benzene derivative having a long, linear conjugated structure prepared in EXAMPLE 1 is maintained at 130° C.

Furthermore, current was measured twice at each voltage while the temperature was maintained at 130° C. FIG. 6 shows the results from the first time, and FIG. 7 shows the results from the second time.

Figure 8:
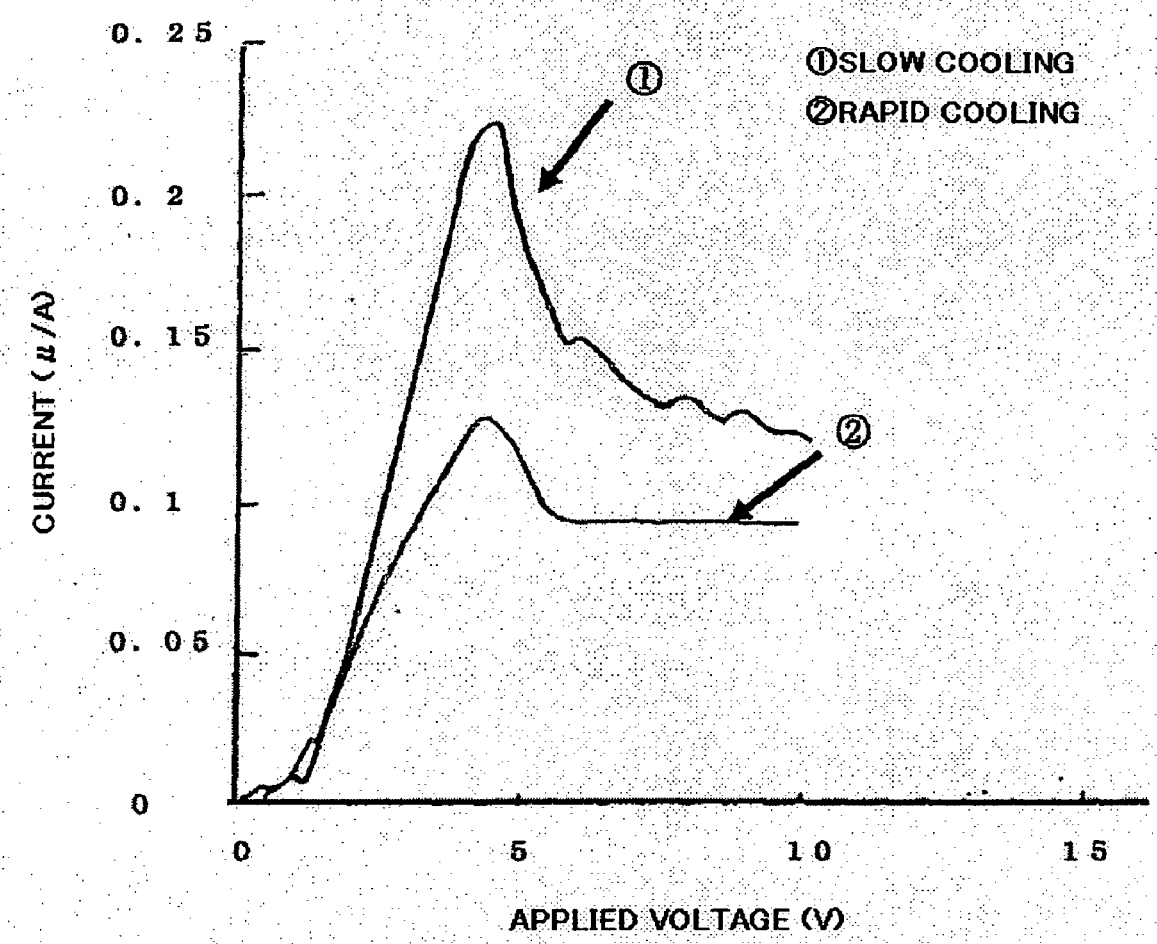
FIG. 8 is a graph showing the relationship between voltage and current at 100° C. after the benzene derivative having a long, linear conjugated structure prepared in EXAMPLE 1 is heated to 130° C. and then naturally cooled to 100° C. and showing the relationship between voltage and current at 100° C. after the benzene derivative having a long, linear conjugated structure prepared in EXAMPLE 1 is heated to 130° C. and then rapidly cooled to 100° C.

Current was measured at each voltage at 100° C. after the temperature was reduced from 130° C. to 100° C. by natural cooling. FIG. 8 shows the results.

Current was measured at each voltage at 100° C. after the temperature was reduced from 130° C. to 100° C. over a period of 10 minutes in a refrigerator (rapid cooling). FIG. 8 shows the results.

Figure 9:
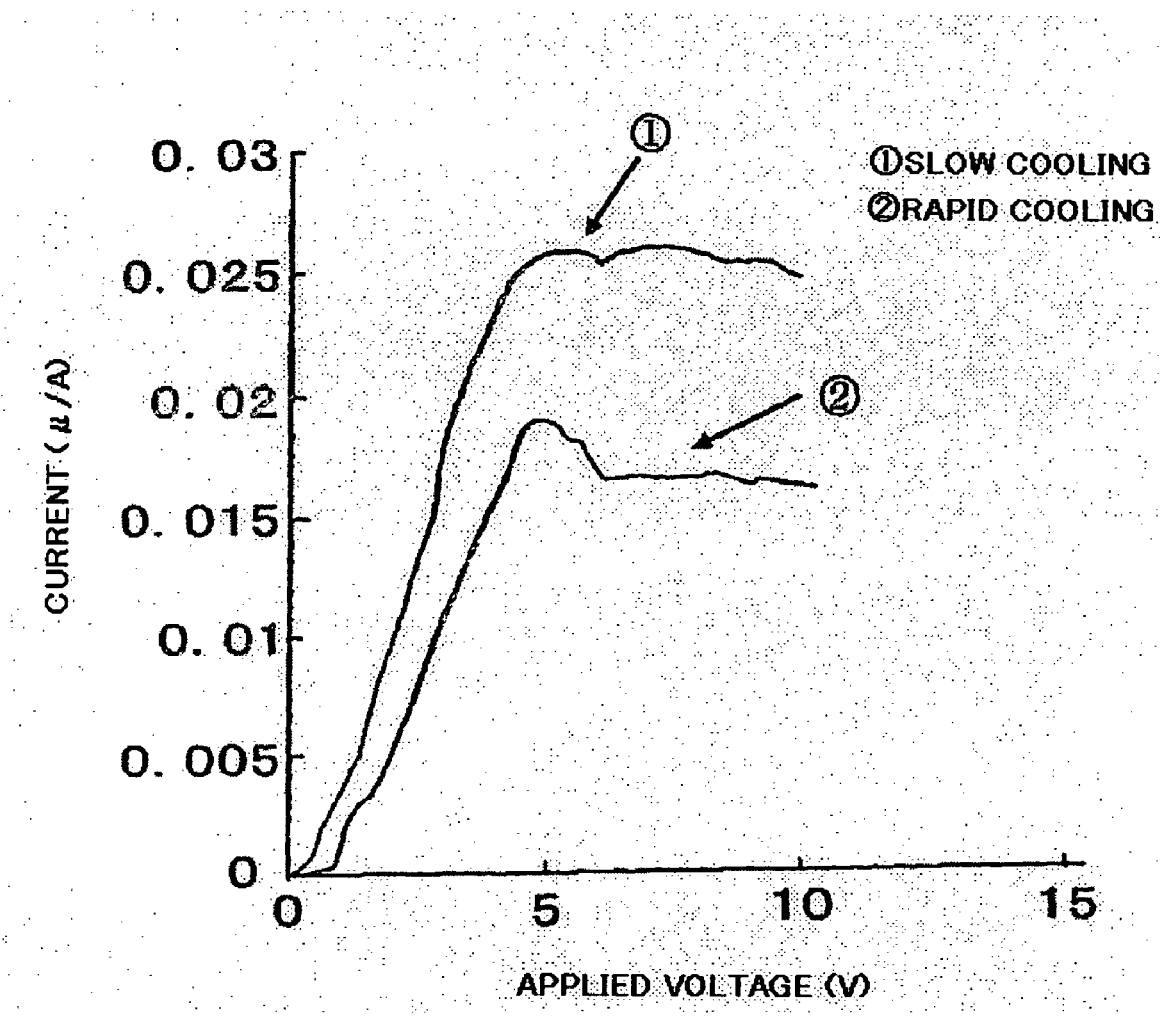
FIG. 9 is a graph showing the relationship between voltage and current at 50° C. after the benzene derivative having a long, linear conjugated structure prepared in EXAMPLE 1 is heated to 130° C. and then naturally cooled to 50° C. and showing the relationship between voltage and current at 50° C. after the benzene derivative having a long, linear conjugated structure prepared in EXAMPLE 1 is heated to 130° C. and then rapidly cooled to 50° C.

Current was measured at each voltage at 50° C. after the temperature was reduced from 130° C. to 50° C. by natural cooling. FIG. 9 shows the results.

Current was measured at each voltage at 50° C. after the temperature was reduced from 130° C. to 50° C. over a period of 10 minutes in a refrigerator (rapid cooling). FIG. 9 shows the results.

INDUSTRIAL APPLICABILITY

As has been described above, an inventive benzene derivative having a long, linear conjugated structure represented by general formula (1) is a novel compound. The benzene derivative having a long, linear conjugated structure is a compound having smectic liquid crystallinity. A charge-transport material containing the benzene derivative having a long, linear conjugated structure or a compound derived from the derivative exhibits a satisfactory ability to transport charge by applying a voltage to the charge-transport material in a state in which molecular orientation of the liquid-crystalline state was maintained. Unlike a known charge-transport material, charge can be transported at a current density of the order of 500 μA/cm² or more and preferably the order of 1 mA/cm² or more. The current density corresponds to $1.6 \times 10^{-7}$ s/cm or more in conductivity, and this value is a value in semiconductor region.

Therefore, by using such charge-transport properties, the inventive charge-transport material can be suitably used in, for example, optical sensors, organic electroluminescent elements (EL elements), photoconductors, spatial modulators, thin-film transistors, charge-transport materials for electrophotographic photoreceptors, photolithography, solar cells, nonlinear optical materials, organic semiconductor capacitors, or other sensors.

The invention claimed is:

1. A benzene derivative having a long, linear conjugated structure represented by general formula (1):

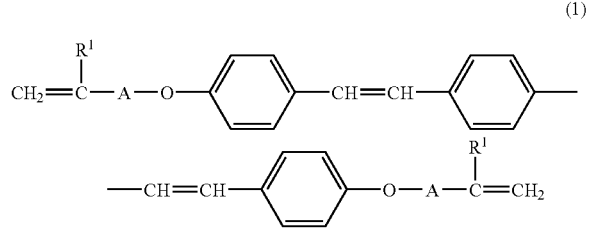

(1)

(wherein $R^1$ represents a methyl group or a hydrogen atom, and A represents an alkylene group,).

2. A process for producing a benzene derivative having a long, linear conjugated structure represented by general formula (1):

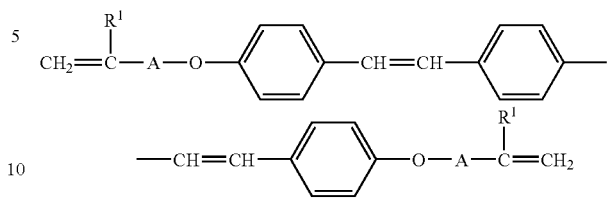

(1)

(wherein $R^1$ and A represents an alkylene group), the process comprising the steps of: allowing 4-hydroxybenzaldehyde represented by general formula (2):

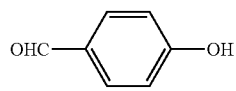

(2)

to react with a halogenated compound represented by general formula (3):

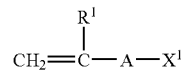

(3)

(wherein $R^1$ and A are the same as described above, and $X^1$ represents a halogen atom), in the presence of a base to produce a benzaldehyde derivative represented by general formula (4):

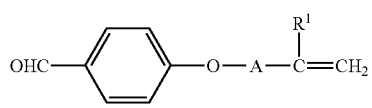

(4)

(wherein $R^1$ and A are the same as described above); and allowing the resulting benzaldehyde derivative to react with a p-xylenebis-(triphenylphosphonium halide) represented by formula (5):

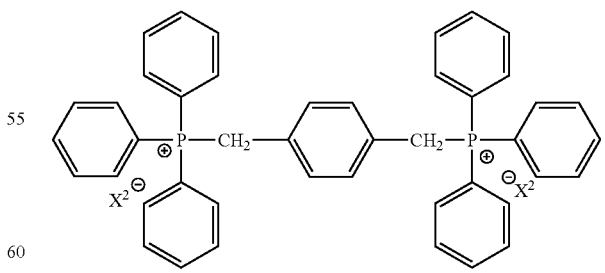

(5)

(wherein $X^2$ represents a halogen atom).

* * * * *